(12) United States Patent
Mizutani et al.

(10) Patent No.: US 6,362,391 B1
(45) Date of Patent: Mar. 26, 2002

(54) DISPOSABLE BODY FLUIDS ABSORBENT ARTICLE

(75) Inventors: Satoshi Mizutani; Etsuko Tagami, both of Kagawa (JP)

(73) Assignee: Uni-Charm Corporation

( * ) Notice: Subject to any disclaimer, the term of this patent is extended or adjusted under 35 U.S.C. 154(b) by 0 days.

(21) Appl. No.: 09/428,065

(22) Filed: Oct. 27, 1999

(30) Foreign Application Priority Data

Oct. 30, 1998 (JP) .............................. 10-309925

(51) Int. Cl.$^7$ ................................. A61F 13/15
(52) U.S. Cl. ................. 604/379; 604/380; 604/385.101
(58) Field of Search ............................... 604/370, 372, 604/379, 380, 385.23, 385.22, 385.101; 156/183, 210; 428/171, 172

(56) References Cited

U.S. PATENT DOCUMENTS

| | | | |
|---|---|---|---|
| 4,443,512 A | * 4/1984 | Delvaux | 428/162 |
| 5,368,926 A | * 11/1994 | Thomson et al. | 428/284 |
| 6,096,016 A | * 8/2000 | Tsuji et al. | 604/378 |

FOREIGN PATENT DOCUMENTS

| | | |
|---|---|---|
| DE | 44 22 956 A1 | 1/1996 |
| EP | 0 686 384 A2 | 12/1995 |
| EP | 0 841 156 A1 | 5/1998 |
| GB | 2 023 067 A | 12/1979 |
| GB | 2 272 917 A | 6/1994 |
| JP | A-7-328061 | 12/1995 |
| WO | WO 97/02133 | 1/1997 |
| WO | WO 98/42290 | 10/1998 |

OTHER PUBLICATIONS

Copy of European Search Report dated Mar. 22, 2001.

* cited by examiner

Primary Examiner—John G. Weiss
Assistant Examiner—Jamisue Webb
(74) Attorney, Agent, or Firm—Baker & Daniels

(57) ABSTRACT

A disposable body fluids absorbent article which includes a topsheet made of nonwoven fabric, the topsheet being formed with a plurality of pleats extending substantially in one direction. Crests and troughs of the pleats have a relatively high density and side walls defined between the crests and the troughs have a relatively low density. The article having such a topsheet enables the absorption capacity of an absorbent core of the article to be utilized as efficiently as possible.

6 Claims, 5 Drawing Sheets

DISPOSABLE BODY FLUIDS ABSORBENT ARTICLE

BACKGROUND OF THE INVENTION

This invention relates to a disposable body fluids absorbent article such as a sanitary napkin or a disposable diaper and more particularly to such an article including a liquid-pervious topsheet formed with a plurality of pleats.

Japanese Patent Application Disclosure Gazette (Kokai) No. Hei7-328061 discloses a sanitary napkin in which a liquid-pervious topsheet is made of a nonwoven fabric formed with a plurality of high density zones and low density zones alternately arranged in a stripe-pattern. The high density zones have their upper surface covered with plastic film. The low density zones are protuberant relatively to the upper surface of the high density zones.

The topsheet of the napkin allows menstrual fluid to spread rapidly toward longitudinally opposite ends of the napkin along the high density zones extending in the stripe-pattern after menstrual fluid has transferred from the low density zones to the high density zones. Accordingly, the napkin allows an absorption capacity of a body fluids absorbent core to be efficiently utilized not only in a central region of the napkin on which menstrual fluid is discharged but also in the longitudinally opposite ends of the napkin.

With the known napkin, the presence of the high density zones enables the absorption capacity of the napkin to be efficiently utilized also in the longitudinally opposite ends thereof. However, the high density zones covered with the plastic film can not directly absorb menstrual fluid and, as a result, a rate of menstrual fluid absorption can not be improved as much as expected from a large surface area of the topsheet.

SUMMARY OF THE INVENTION

It is an object of the present invention to utilize an absorption capacity of a disposable body fluids absorbent article such as a sanitary napkin as efficiently as possible without deteriorating a rate of body fluids absorption.

According to the present invention, there is provided a disposable body fluids absorbent article including a body fluids absorbent core having a surface thereof at least partially covered with a liquid-pervious sheet of nonwoven fabric, the nonwoven fabric being partially formed with a plurality of alternately arranged high density zones and low density zones extending substantially in one direction. The topsheet is formed by thermoplastic synthetic fibers having a basis weight of 20~80 g/m² and formed with a plurality of pleats extending in the one direction, the pleats repeating undulation transversely of the one direction, the high density zones being defined by crests and troughs of the pleats and the low density zones being defined between the crests and troughs, and the troughs being in contact with a surface of the absorbent core.

According to one embodiment of the present invention, a depth from the crest to the trough of the pleat is 1~10 mm and a distance between each pair of adjacent crests is 1~15 mm.

According to another embodiment of the present invention, a density of the high density zone is 0.08~0.25 g/cm³.

According to still another embodiment of the present invention, a width of the high density zone is 0.5~3 mm.

According to further another embodiment of the present invention, the high density zones continuously extend in the one direction.

According to an additional embodiment of the present invention, the high density zones intermittently extend in the one direction.

DETAILED DESCRIPTION OF THE PREFERRED EMBODIMENTS

Details of a disposable body fluids absorbent article according to the present invention will be more fully understood from the description given hereunder with reference to the accompanying drawings.

Figure 1:
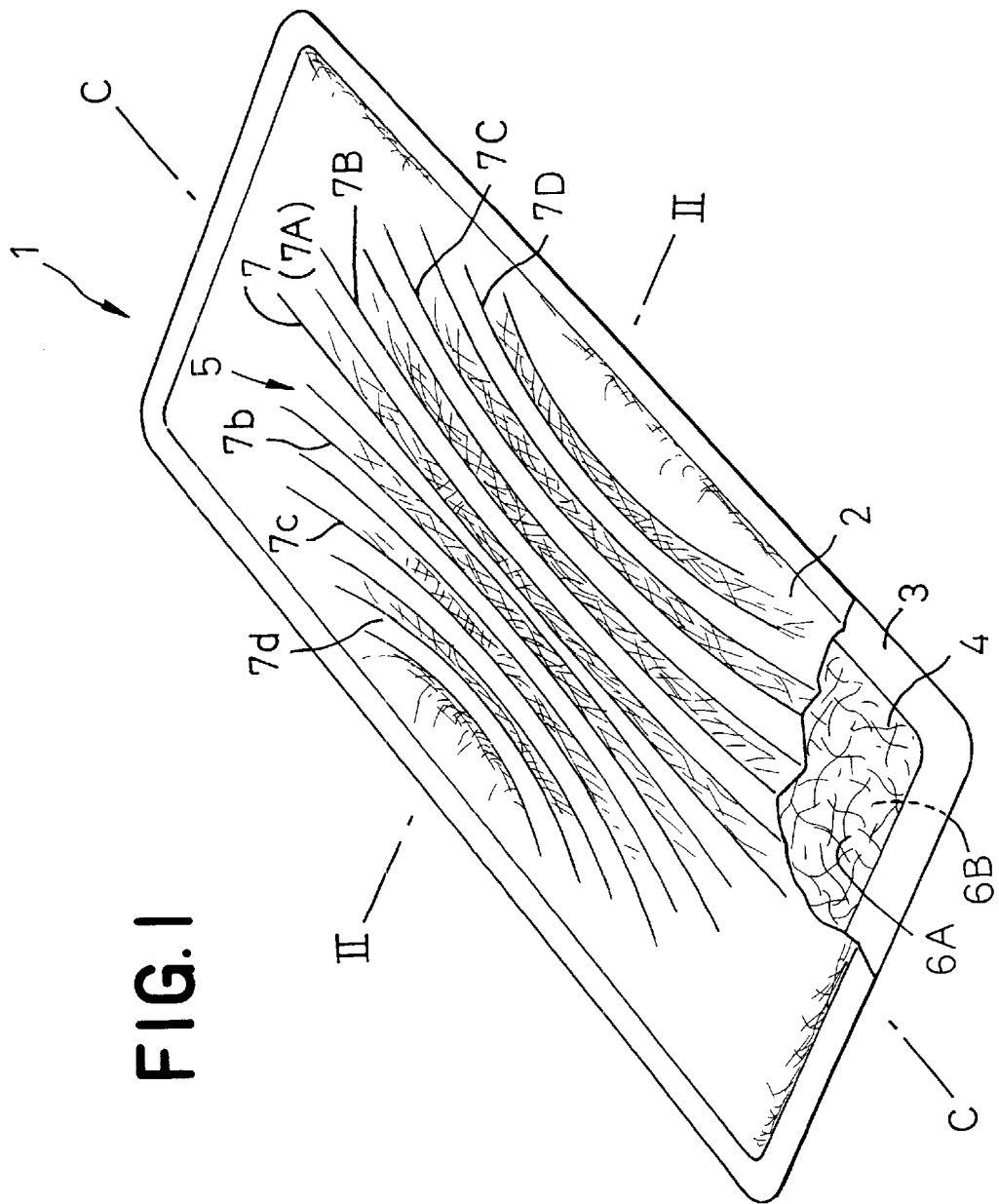
FIG. 1 is a perspective view showing a sanitary napkin according to a specific embodiment of the present invention as partially broken away.

A napkin 1 shown by FIG. 1 in a perspective view as partially broken away is larger in its longitudinal direction and includes a liquid-pervious topsheet 2, a liquid-impervious backsheet 3 and a liquid-absorbent core 4 having its upper and lower surfaces 6A, 6B covered with these two sheets 2, 3, respectively. The topsheet 2 and the backsheet 3 are placed upon and bonded to each other along their portions extending outward beyond a peripheral edge of the core 4.

The topsheet 2 is formed by a nonwoven fabric made of thermoplastic synthetic fibers and provided with a plurality of pleats 5 arranged symmetrically with respect to a center line C—C dividing a width of the napkin 1 in two. The pleats extend substantially in the longitudinal direction of the napkin 1. More exactly, of crests 7 of these pleats 5, a crest 7A extending just above the center line C—C is rectilinear and crests 7B, 7C, . . . and crests 7b, 7c, . . . extending symmetrically with respect to the center line C—C are gently curved. These curved crests 7B, 7C, . . . and 7b, 7c, . . . are formed so that they progressively become shorter as they go far off from the center line C—C.

Figure 2:
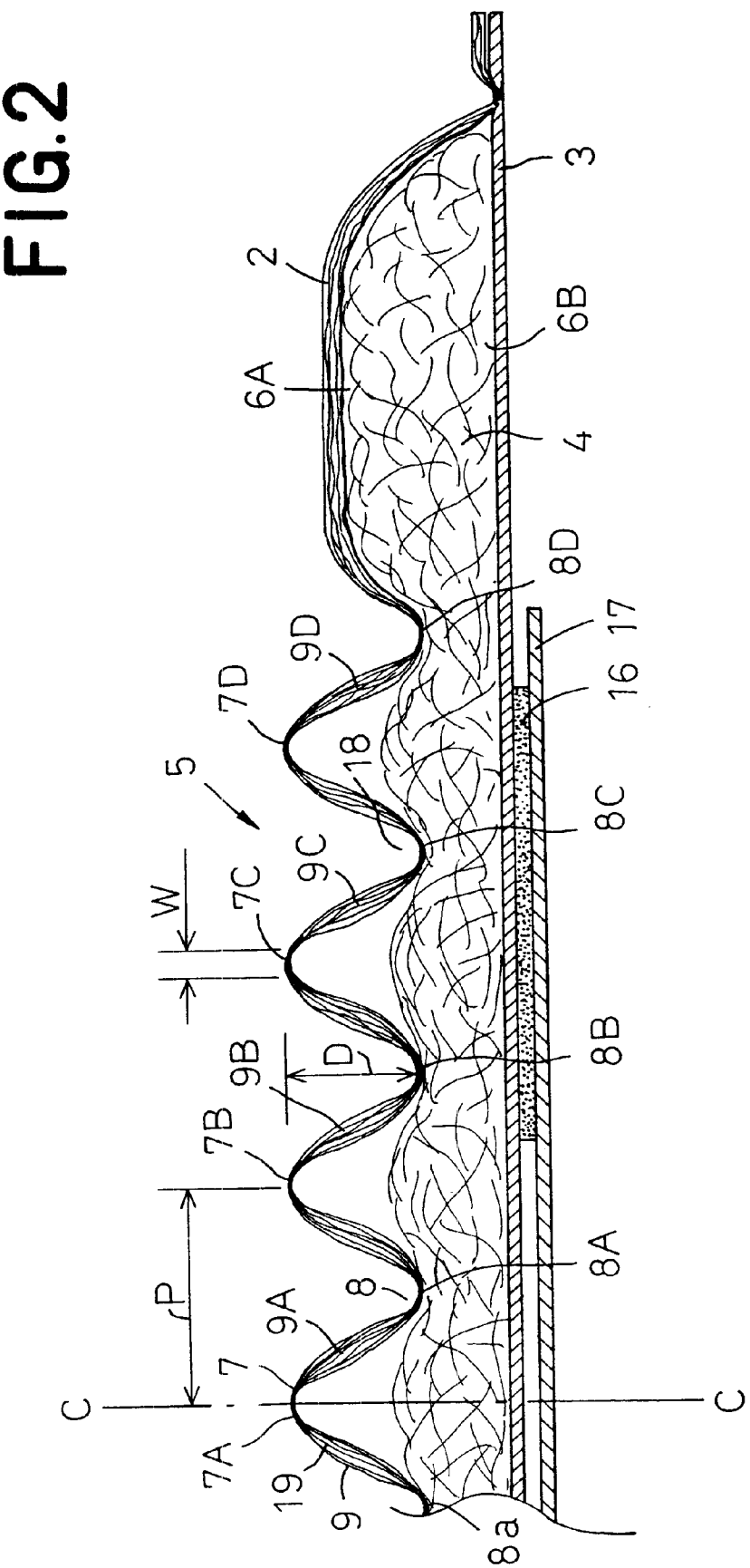
FIG. 2 is a fragmentary sectional view taken along a line II—II in FIG. 1.

FIG. 2 is a fragmentary sectional view taken along a line II—II in FIG. 1. The pleats 5 of the topsheet 2 have, in addition to the crests 7 (7A, 7B, 7C, . . . , 7b, 7c, . . . ), troughs 8 (8A, 8B, . . . , 8b, 8c, . . . ) and side walls 9 (9A, 9B, . . . , 9a, 9b, . . . ) extending between the crests 7 and the troughs 8, respectively. The nonwoven fabric forming the topsheet 2 have been firmly compressed at the crests 7 and troughs 8 under heating or not under heating. Consequently, the nonwoven fabric is relatively thin and has a relatively low density at these crests 7 and troughs 8. The side walls 9 have been substantially not compressed or slightly compressed. Therefore, the nonwoven fabric is relatively thick and has a relatively low density at these side walls 9. A distance between each pair of adjacent crests 7 in the pleats 7 is herein represented by P and a depth from the crests 7 to the troughs 8 is herein represent by D.

The nonwoven fabric as stock material for the topsheet 2 may be selected from a spun bond nonwoven fabric or a melt bond nonwoven fabric or the like made of suitable synthetic fibers such as of polyethylene, polypropyrene, nylon or polyester. However, a nonwoven fabric made of conjugated fibers, particularly of crimped conjugated fibers is more preferable as the stock material for the topsheet 2. Preferably, such nonwoven fabric has a fineness of 1~6 deniers, a basis weight of 20 ~80 g/m² and a density of 0.025~0.05 g/cm³. The pleats 5 formed by the nonwoven fabric is defined by the distance P between each pair of adjacent crests 7 preferably of 1~15 mm, more preferably of 2~10 mm and the depth D from the crests 7 to the troughs 8 preferably of 1~10 mm, more preferably of 1~6 mm. The density at the crests 7 as well as at the troughs 8 is preferably as high as 0.08~0.25 g/cm³ particularly along a width of 0.5~3 mm.

The core having its upper surface 6A covered with the topsheet 2 comprises fluff pulp or a mixture of fluff pulp and superabsorptive polymer particles. The core 4 is in contact with the pleats 5 defined by the crests 7, the troughs 8 and the side walls 9, with at least the troughs 8, and preferably also the inner surfaces of the respective side walls in contact with the core 4 as shown more preferably with the inner surfaces of the respective crests 7 also in contact with the core 4. Along a peripheral region of the napkin 1 surrounding the pleats 5, the core 4 is also in contact with the inner surface of the topsheet 2. The core 4 and the topsheet 2 may be locally bonded to each other by means of a suitable adhesive agent such as hot melt adhesive or by a heat-sealing technique in order to ensure that the core 4 is kept in contact with the topsheet 2.

The backsheet 3 covering the lower surface 6B of the core 4 is formed from a plastic film and is bonded to the topsheet 2 along its peripheral edge by means of a suitable adhesive agent or by a sealing technique. The backsheet 3 is applied on its lower surface with suitable adhesive agent 16 by which the napkin 1 is separably fastened to the shorts worn by a napkin wearer and the adhesive agent 16 is covered with a release paper sheet 17.

With the napkin 1 put on the wearer's body, a portion of menstrual fluid discharged on a central zone of the napkin 1 is absorbed by the crests 7 of higher density, then spread along the crests 7 toward longitudinally opposite ends of the napkin 1 and from there the menstrual fluid is absorbed into the core 4. The remainder of menstrual fluid flowing down along the side walls 9 toward the troughs 8 of the pleats 5 is rapidly absorbed by the troughs 8 of higher density and then immediately transferred to the core 4, or spreaded along the troughs 8 toward the opposite ends of the napkin 1 before absorbed into the core 4. Menstrual fluid can flow relatively freely along the troughs 8 of the pleats 5 toward the longitudinally opposite ends of the napkin 1. In this manner, the napkin 1 allows menstrual fluid to flow rapidly from its central zone toward the longitudinally opposite ends and thereby allows an absorption capacity of the longitudinally larger core 4 to be utilized as efficiently as possible. On the other hand, a transverse flow of menstrual fluid is obstructed by the side walls 9 of the pleats 5 and therefore, there is no apprehension that a portion of menstrual fluid might leak sideways. For the napkin which is generally configured to be larger in its longitudinal direction, it is an important feature of the napkin 1 according to the present invention, from the viewpoint of preventing menstrual fluid from leaking sideways, that the napkin 1 can facilitate menstrual fluid transfer in the longitudinal direction but restrain menstrual fluid from transferring in the transverse direction.

Figure 3:
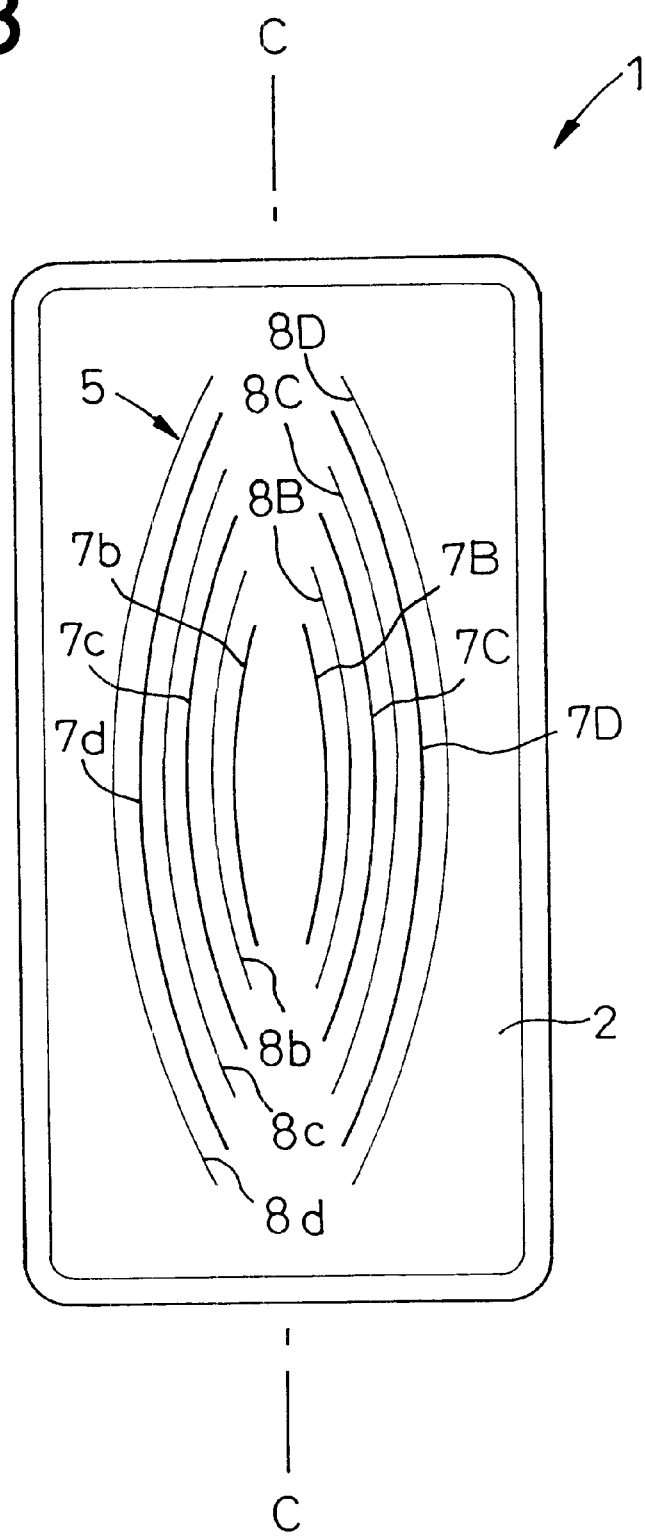
FIG. 3 is a plan view a sanitary napkin according to one preferred embodiment of the present invention.
Figure 4:
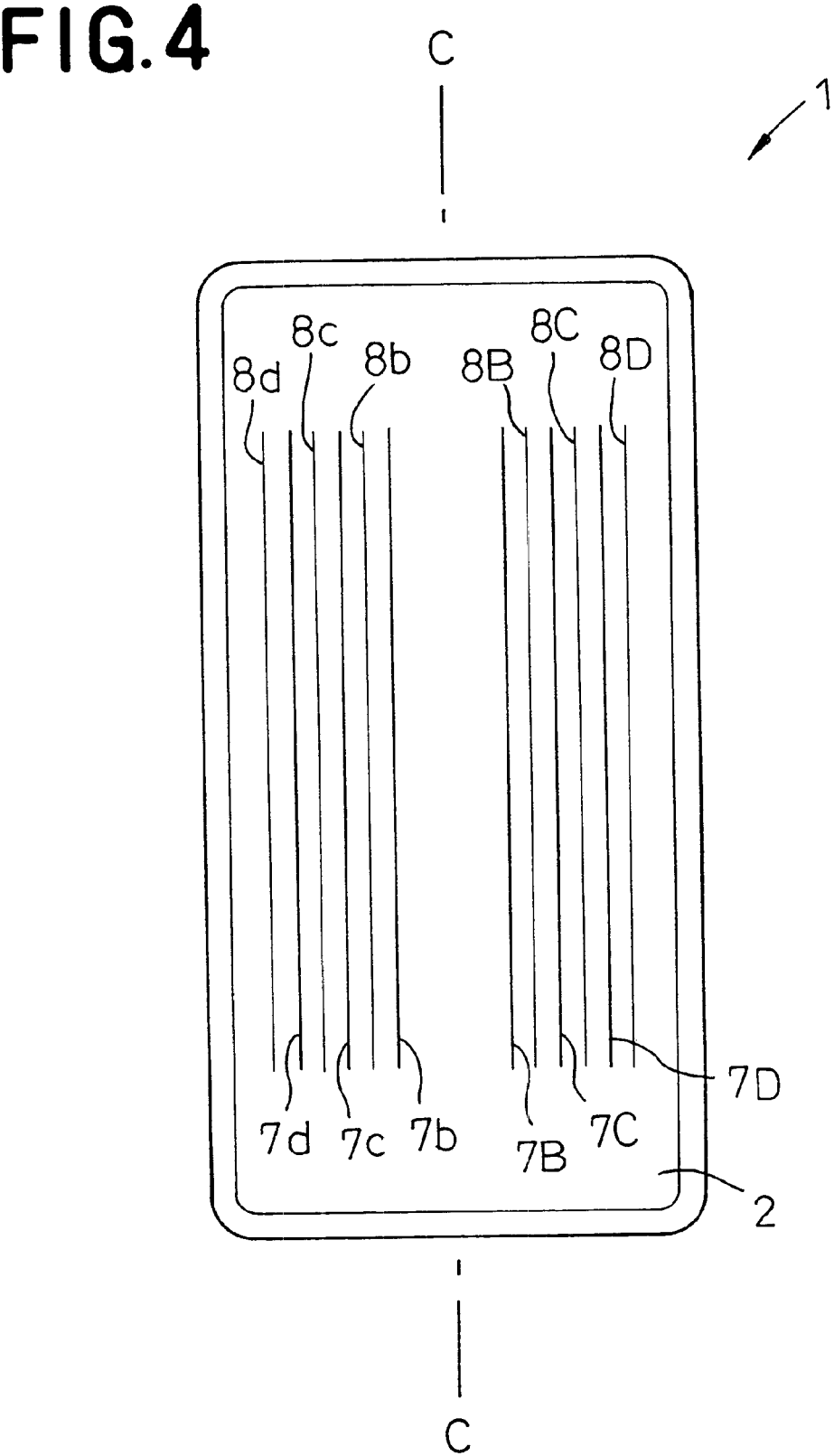
FIG. 4 is a view similar to FIG. 3, showing a sanitary napkin according to still another preferred embodiment of the present invention.
Figure 5:
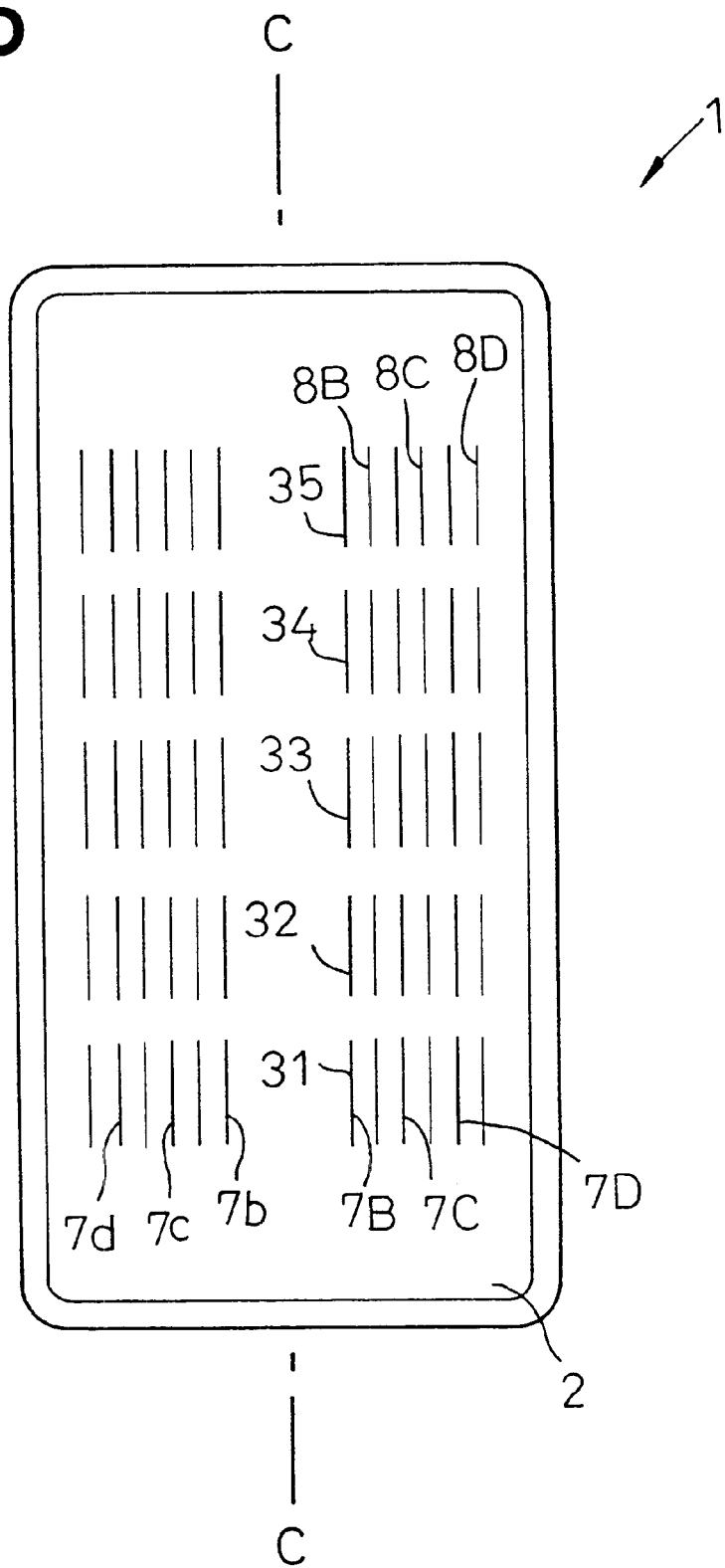
FIG. 5 is a view similar to FIG. 3, showing a sanitary napkin according to further another preferred embodiment of the present invention.

FIGS. 3, 4 and 5 are plan views showing preferred embodiments of the napkin 1 according to the present invention. In the case of the napkin 1 shown in FIG. 3, symmetrically with respect to the center line C—C the topsheet 2 is formed with a plurality of pleats 5 having the crests 7B, 7C, . . . , 7b, 7c, . . . and the troughs 8B, 8C, 8b, 8c, . . . extending in parallel to the troughs substantially in the longitudinal direction of the napkin 1. More exactly, these pleats 5 are gently curved toward the center line C—C and progressively become longer as they go far off from the center line C—C. In the case of the napkin 1 shown in FIG. 4, the crests 7B, 7C, . . . , 7b, 7c, . . . and the troughs 8B, 8C, . . . , 8b, 8c, . . . defining the respective pleats 5 extend in parallel one to another as well as to said center line C—C and longitudinal dimensions of the respective crests are uniform. The napkin 1 shown in FIG. 5 is similar to the napkin 1 shown in FIG. 4 except that the crests 7B, 7C, . . . , 7b, 7c, . . . and the troughs 8B, 8C, . . . 8b, 8c, . . . continuously extending between the longitudinal opposite ends of the napkin 1 shown in FIG. 4 are respectively divided into short sections in the case of the napkin 1 shown in FIG. 5. For example, the crest 7B extending in parallel to the center line C–C comprises a plurality of relatively short crests 31, 32, 33, . . . intermittently arranged in the longitudinal direction. Each of these short crests 31, 32, 33, . . . preferably has a length of 1~10 mm and a distance between each pair of adjacent crests 31, 32, 33, . . . is preferably 0.3~1 mm. By dividing the crests as well as the troughs in this manner, the napkin 1 can be flexibly curved along a crotch region of the shorts worn by the napkin wearer. The distance between each pair of adjacent crests of each pleat 5 is sufficiently small to ensure that menstrual fluid can rapidly spread in the longitudinal direction.

To realize the present invention, the topsheet 2 may be formed from a hydrophilic nonwoven fabric or a hydrophobic nonwoven fabric. When a hydrophobic nonwoven fabric is used, the crests 7 and the troughs 8 may be locally treated to become hydrophilic. The topsheet 2 as has been described above in the connection with the sanitary napkin 1 as a specific embodiment of the present invention can be used also as the topsheet for the other various disposable body fluids absorbent articles such as disposable diaper and shorts for incontinent patient.

The disposable body fluids absorbent article according to the present invention allows body fluids to spread along the pleats formed on the topsheet, particularly along the crests and the troughs thereof both having relatively high densities to the longitudinally opposite ends of the napkin. Accordingly, the absorption capacity of the core can be utilized as efficiently as possible so that much amount of body fluids may be absorbed and undesirable leakage of body fluids may be effectively avoided. The pleats function to prevent body fluids from flowing transversely thereof and improve prevention of body fluids from leaking sideways. The troughs have a relatively high density promote body fluids to transfer from the crests toward the troughs. Furthermore, pleats provide a surface area of the garment serving to absorb body fluids larger than such surface area provided by the flat topsheet and thereby improve a rate of body fluids absorption. The pleats not only contribute to improvement in body fluids absorbing ability of the napkin but also make the topsheet cushiony and provide the article according to the present invention with a soft touch.

What is claimed is:

1. A disposable body fluids absorbent article comprising:
   a body fluids absorbent core; and
   a liquid-pervious sheet of nonwoven fabric covering at least a portion of the surface of the absorbent core, said liquid-pervious sheet of nonwoven fabric being formed with a plurality of alternately arranged high density zones and low density zones extending substantially in one direction, said nonwoven fabric being formed from thermoplastic synthetic fibers having a basis weight of 20~80 g/m$^2$ and formed with a plurality of pleats extending in said one direction, said pleats repeating in an undulatory manner transversely of said one direction, said high density zones being defined by crests and troughs of said pleats and said low density zones defined between said crests and troughs, said troughs being in contact with the surface of said core.

2. The disposable body fluids absorbent article according to claim 1, wherein a depth measured between a crest and a trough of said pleats is about 1 to about 10 mm and a distance between pairs of adjacent ones of said crests is about 1 to about 15 mm.

3. The disposable body fluids absorbent article according to claim 1, wherein a density of said high density zones is about 0.08 to about 0.25 g/cm$^3$.

4. The disposable body fluids absorbent article according to claim 1, wherein a width of said high density zones is about 0.5 to about 3 mm.

5. The disposable body fluids absorbent article according to claim 1, wherein said high density zones extend in a continuous manner along said one direction.

6. The disposable body fluids absorbent article according to claim 1, wherein said high density zones extend intermittently along said one direction.

* * * * *